United States Patent [19]

Bellare et al.

[11] Patent Number: 4,753,887
[45] Date of Patent: Jun. 28, 1988

[54] CONTROLLED ENVIRONMENT VITRIFICATION SYSTEM FOR PREPARATION OF LIQUIDS

[75] Inventors: Jayesh R. Bellare, Bombay, India; Howard T. Davis; L. Edward Scriven, II, both of Minneapolis, Minn.; Yeshayahu Talmon, Haifa, Israel

[73] Assignee: Regents of the University of Minnesota, Minneapolis, Minn.

[21] Appl. No.: 894,302

[22] Filed: Aug. 7, 1986

[51] Int. Cl.⁴ .............................................. C12M 1/00
[52] U.S. Cl. .................................... 435/287; 435/290; 62/64
[58] Field of Search ............... 435/287, 289, 290, 292, 435/294, 299, 300, 313; 62/55.5, 62, 64, 514 R

[56] References Cited

U.S. PATENT DOCUMENTS

| | | | |
|---|---|---|---|
| 4,090,921 | 5/1978 | Sawamura et al. | 435/290 |
| 4,209,585 | 6/1980 | Lloyd et al. | 435/287 |
| 4,304,293 | 12/1981 | Scheiwe et al. | 435/290 |
| 4,489,569 | 12/1984 | Sitte | 62/514 R |
| 4,578,963 | 4/1986 | Sitte | 62/514 R |
| 4,580,416 | 4/1986 | Sitte | 62/514 R |
| 4,676,070 | 6/1987 | Linner | 62/64 |
| 4,680,945 | 7/1987 | Hoffmeister | 62/514 R |

OTHER PUBLICATIONS

Adrian et al., "Cryo-Electron Microscopy of Viruses", Nature, vol. 308, No. 5954, pp. 32-36 (Mar. 1984).
Reichert Scientific Instruments Division of Warner Lambert Technologies Inc., Model KF80 Immersion Cryofixation System according to Sitte.

Primary Examiner—Samuel Scott
Assistant Examiner—H. A. Odar
Attorney, Agent, or Firm—Kinney & Lange

[57] ABSTRACT

A system for preparing specimens in a controlled environment to insure that a liquid or partially liquid specimen is maintained in its original state while it is being prepared, and once prepared the specimen is vitrified or solidified with minimal alteration of its microstructure. The controlled environment is provided within a chamber where humidity and temperature can be controlled precisely while the specimen is prepared. The specimen is mounted on a plunger and a shutter controlled opening is opened substantially simultaneously with release of the plunger so the specimen is propelled through the shutter into an adjacent cryogenic bath.

20 Claims, 3 Drawing Sheets

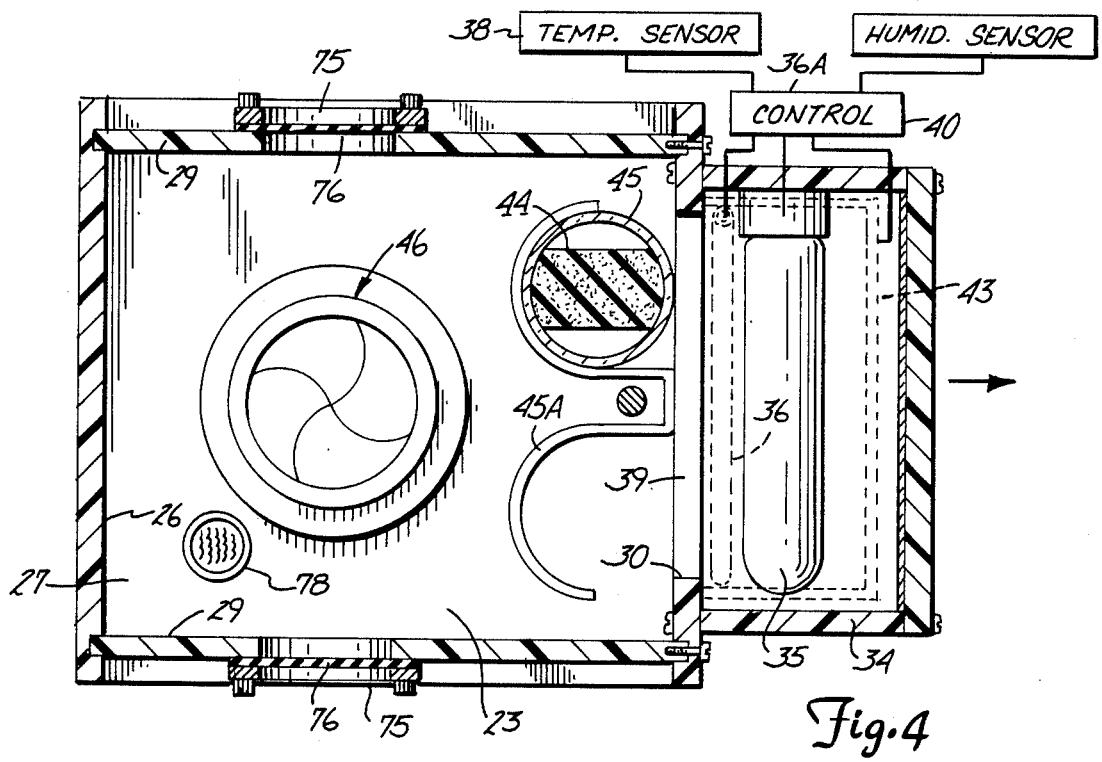
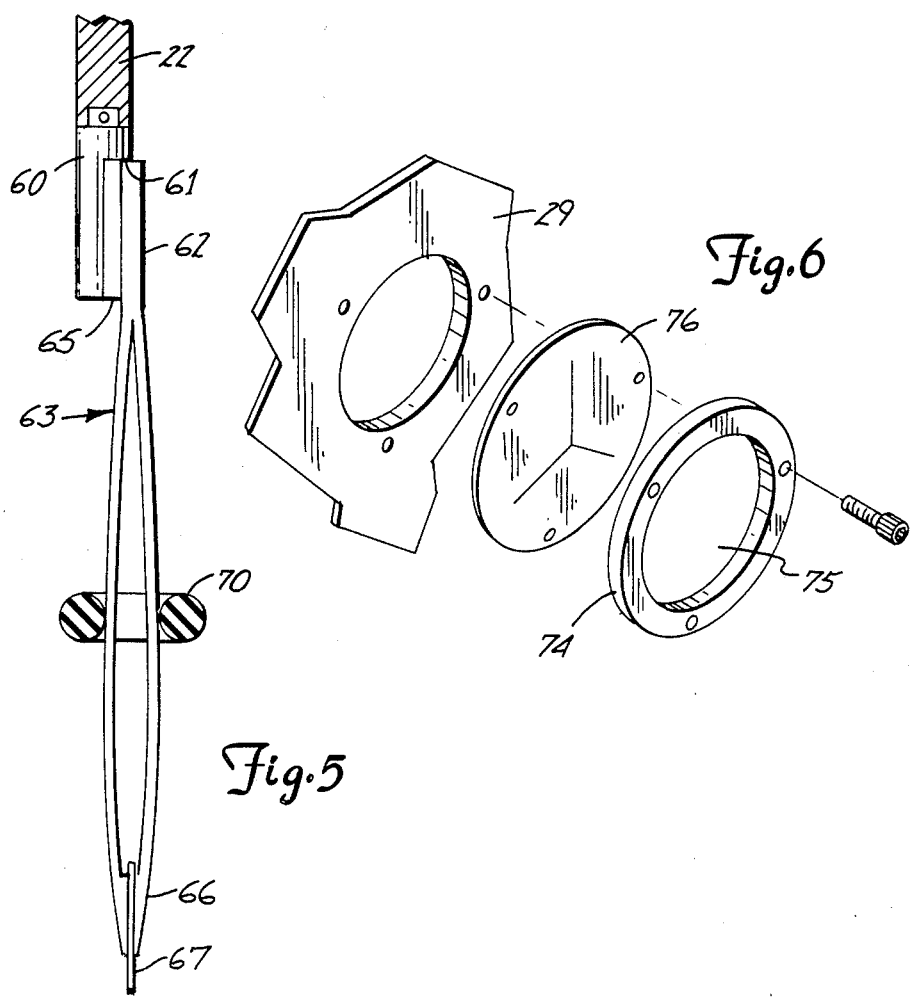

CONTROLLED ENVIRONMENT VITRIFICATION SYSTEM FOR PREPARATION OF LIQUIDS

The invention described herein was made in the course of work under Contract No. DE-AC19-78BC10116 from the Department of Energy, and Grant No. CPE-8215342 awarded by the National Science Foundation. The U.S. government has certain rights in this invention.

BACKGROUND OF THE INVENTION

1. Field of the Invention.

The present invention relates to the preparation of liquid specimens by vitrification for examination of microstructure which includes morphology (size, shape, form), connectivity, topography and texture, by electron microscopy.

2. Description of the Prior Art.

Vitrification as used herein means rapidly cooling a liquid without crystallization into a highly viscous, low vapor pressure, glassy state. Vitrification is an important technique for electron microscopy of frozen hydrated biological and colloidial dispersions and aggregates.

The specimen preparation procedure prior to vitrification consists of the following steps: a specimen support plate (typically a transmission electron microscopy grid) is held by a tweezer mounted on a plunger. A drop of liquid sample to form the specimen is placed on the support plate and most of the liquid is removed by touching the liquid sample on the support plate with a blotting paper or other absorbant material to leave a very thin film of liquid on the support plate. Next, the vitrification process is carried out by allowing the specimen support plate to plunge under the force of gravity into a cooling medium (cryogen), typically melting ethane. This procedure in the prior art was done in an open laboratory atmosphere where temperature and concentration of gasses and vapors cannot be controlled.

The preparation of biological samples for electron microscopy by a vitrification technique is discussed by Adrian et al. in an article entitled "Cryo-Electron Microscopy of Viruses", Nature, Vol. 308, No. 58-54, pgs. 32-36, 1984. The value of rapidly cooling and vitrifying the samples is illustrated.

In preparing samples prior to vitrification, it has been found that when using previously established techniques, preserving the morphology, component chemical potential and connectivity, topography and texture similar to the native state of the sample is extremely difficult. Thus, specimens prepared in an uncontrolled laboratory atmosphere are subject to evaporation, which concentrates solutions and suspensions as much as three fold, and also the specimens are subject to temperature changes. These actions change the chemical potentials of the system components and can result in change of phase (for example precipitation of solids from solution) and change in microstructure.

There are instruments that have been used to attempt to vitrify liquid specimens. For example, the Reichert Scientific Instruments Division of Warner Lambert Technologies Inc. of Buffalo, N.Y. 14240 sells a model KF80 Immersion Cryofixation System. However, this system primarily maintains the cryogens that are used for vitrifying the specimen, and does not provide for preparation of the sample in a controlled atmosphere or environment prior to immersion into a cryofixation medium.

SUMMARY OF THE INVENTION

The present invention relates to preparation of samples or specimens, including aqueous solutions and suspensions, for examination by electron microscopy or by other types of microscope inspection. The present system permits preparation of specimens or samples having appreciable vapor pressure in a way that the microstructure can be examined under low pressure conditions. This is important in many technological fields including but not limited to study of colloids, surfactant dispersions, polymers, viruses, biological cells, foams and emulsions, particulate suspensions, sols, gels, ceramics, microelectronic elements and assemblies, fluid phase reaction systems, nucleation, and phase separation and catalysis. Liquids in their native state cannot be conveniently examined by electron microscope because of high vacuum in an electron microscope. Vitrification of liquid components of systems, followed by cold stage electron microscopy permits examining the microstructure of a specimen unchanged or very little change from the native microstructure of the original liquid sample. However, specimen preparation in an uncontrolled environment causes evaporation and temperature changes that may lead to artifact formation (change in morphology, connectivity, topography or texture) and phase changes. It should be noted that artifact formation may also be caused by mechanical stresses imposed during preparation of the thin sample film on the specimen support plate.

The present invention provides a way of preparing samples of all types of liquid systems, but it is especially advantageous for systems which are highly susceptible to artifact formation. Reduction of artifact formation is accomplished by controlling component chemical potentials and thus the present invention is highly advantageous for systems near a thermodynamic phase boundary, that is, particularly susceptible to phase separation. The present invention includes means which permit specimen or sample preparation at temperatures substantially different from ambient. The present invention permits extended holding of the thin film specimen in an environmental chamber, prior to vitrification, to allow reequilibration of the samples from effects of mechanical stresses induced during thinning.

The present invention comprises an environmental chamber in which the specimens or samples are prepared. The chamber atmosphere can be saturated with one or more chemical components if desired, and its temperature can be closely controlled, to avoid component chemical potential changes in the sample and reduce artifact formation and prevent phase change of the specimen. The environmental chamber has controlled means for saturating the atmosphere in the chamber with desired gases or liquid vapors, and has a temperature controlled heater and cooler for changing and controlling the chamber temperature while the specimen is being prepared. Suitable thermal sensing elements (thermistors or thermocouples for example) and a temperature controller to regulate the power to the heater or cooler are used. The temperature can be measured at several points inside the chamber if desired. Likewise, humidity or vapor saturation inside the chamber can be measured with suitable sensors, such as existing capacitive thin film sensors, and the measurements used to automatically control the environment in a desired manner.

The walls of the environmental chamber are formed to include suitable clear material so that the interior of the chamber can be viewed. The chamber has an access door which can be opened for placing a specimen holder onto a plunger shaft that is slidably mounted in the compartment in registry with a camera shutter on the lower wall of the chamber. The camera shutter is aligned with and is spaced slightly above a container of cryogenic material into which the specimen or sample is to be plunged. The lower end of the plunger shaft as shown in the accompanying drawings is adapted to hold a tweezer which in turn holds a specimen grid or support plate. When the tweezer and specimen support plate are properly positioned, the access door to the environmental chamber is manually closed, and then the atmosphere in the chamber is controlled to reach its desired state of temperature and gas and vapor content. The specimen or sample is introduced using a pipette operated through a split rubber septum to reduce changes in chamber temperature and atmosphere composition. The liquid sample is placed on the specimen support plate and is blotted to form a very thin film. Alternatively, spontaneously wetting films may be formed on the specimen support plate. The chamber atmosphere is controlled to insure that the film will not change. The specimen or sample is thus prepared completely within a chamber having a controlled environment so the specimen remains representative of the original liquid sample.

When the specimen has been prepared, a cryogenic bath, which preferrably is melting ethane or alternatively, propane or selected freons, maintained in a liquid nitrogen bath, in an insulated container is positioned below the shutter that is in the bottom wall of the environmental chamber. A double cable release with a single actuator button is used for first releasing the plunger shaft and after a selected very small time delay quickly opening the camera shutter so that the shaft and specimen support plate plunges through the shutter opening and the specimen is dropped under provided force (gravity or a spring load, for example) without any opportunity for evaporation or change in the state of specimen on the specimen support plate prior to vitrification.

A self-cocking photographic camera shutter, such as a Prontor shutter is used. This is an iris type shutter that opens quickly and can be kept closed until desired, to enable retaining environmental control and preventing the specimen from being precooled by the cold cryogen vapors that are directly below this shutter. The use of a double cable release to trip the mechanism including the plunger or shaft that plunges the specimen into the cryogen material and subsequently opens the shutter, permits precise timing by adjusting the length of the cable release pins.

The plunger shaft is held in place before plunging with a releasable pin that is moved by operation of the cable release.

The specimen or sample is then handled in a desired manner and transferred to the electron microscope for examination.

BRIEF DESCRIPTION OF THE DRAWINGS

FIG. 4 is a sectional view taken as on line 4—4 in FIG. 1 with certain parts illustrated in phantom lines;

FIG. 5 is a side view of a specimen support plate holding tweezer with parts in section;

FIG. 6 is an exploded view of a septum assembly used for inserting a specimen or sample into the environmental chamber.

DETAILED DESCRIPTION OF THE PREFERRED EMBODIMENTS

Figure 3:
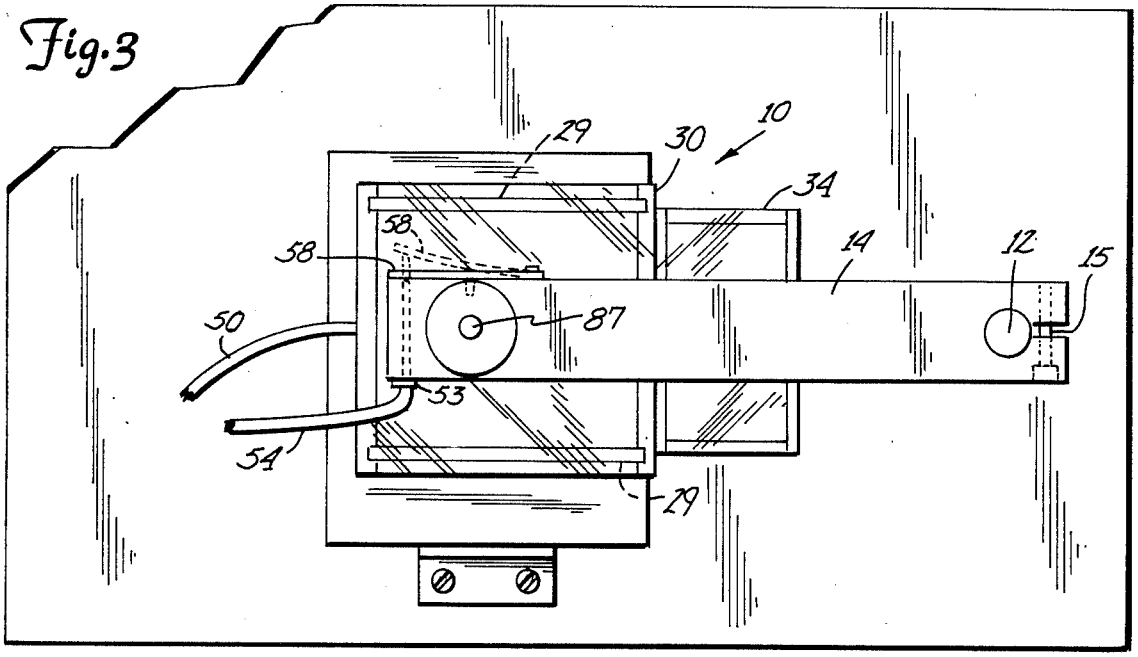
FIG. 3 is a top plan view thereof.
Figure 2:
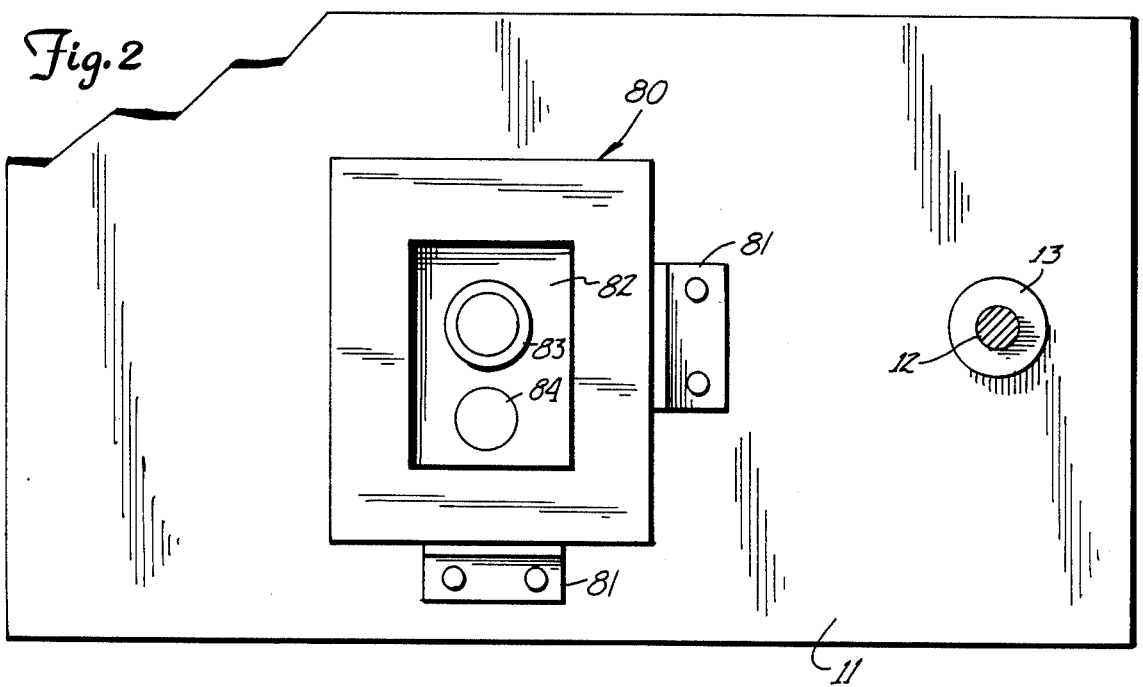
FIG. 2 is a top plan view of a cryogenic container used with the vitrification apparatus.

A controlled environment vitrification apparatus illustrated generally at 10 comprises a laboratory instrument that can be used for vitrification of liquid samples or specimens, and includes a base plate or frame 11, and an upright post 12 mounted in a suitable bushing 13 that is attached to the base plate 11. The post 12 in turn mounts a cantilever arm 14 that is clamped in place on the post 12 with a split clamp arrangement 15 (FIG. 3) at one end. The arm 14 is held clamped onto the post with a clamp screw 16 at the desired height. The cantilever arm 14 forms a main support for an environmental chamber housing indicated generally at 20. The environmental chamber housing 20 has a top wall 21 that is attached to the lower side of the cantilever arm 14. The top wall 21 has an opening to permit a plunger shaft 22 to pass into the interior environmental chamber 23 (FIG. 4). The plunger shaft 22 is slidably mounted for movement along its longitudinal axis in a suitable low friction bearing or bushing indicated generally at 25 that is mounted in the cantilever arm 14.

The environmental chamber housing 20 has a front wall 26 connected to the top wall 21, and a bottom wall 27 fixed to the lower edge of the front wall 26. The top wall, front wall and bottom wall are formed as a frame, on which a sliding housing cover section assembly 28 is supported. This sliding housing section comprises a pair of spaced side walls 29 and a rear wall 30. The upper and lower edges of side walls 29 are slidably mounted in grooves formed in the top wall 26 and bottom wall 27. The sliding housing section can be slid rearwardly toward the upright post 12 to permit access to the interior chamber 23, as can be seen in dotted lines in FIG. 1. The housing 20 is made to be adequately sealed to permit controlling the atmosphere in the chamber 23. The housing section 28 of the environmental chamber can be slid rearwardly for loading a specimen holder plate into position and for performing other tasks where access to the environmental chamber is required. The walls of the housing 20 are all made of transparent material, such as a polycarbonate.

The housing section 28 includes a rear housing 34 that houses a heater 35 which can comprise a quartz lamp, that is directed to the interior chamber 23, and a cooler 36 (a Peltier effect cooler is preferred). A Peltier effect cooler also can act as a heater when current is reversed. The heat from the heater 35 and/or the cooling or refrigeration from cooler 36 can be controlled by controlling the applied voltage in response to one or more suitable temperature sensors 38. The sensors 38 can be thermistors operated in a known manner and can be located in selected areas of the chamber to insure that the chamber temperature is controlled in a desired manner and that the temperature is substantially uniform.

A control circuit indicated schematically at 40 is used to turn on and control the heater 35 or the cooler 36 as needed. The control circuit 40 is shown schematically and is well known. The heat or cooling that is provided can be directed to a particular area of the chamber 23 so that there can be a desired temperature maintained uniformly across the entire chamber. The heater 35 aligns with an opening 39 in the rear wall 30. The cooler 36 is adjacent the upper portion of the rear housing 34 and there is an opening 41 shown in FIG. 1 leading from a fan box 43 that houses a fan 42. The fan box is configured to minimize vortex formation and to provide a relatively uniform environment in the chamber.

The fan 42 is operated to direct a flow of air into the environmental chamber 23 through opening 41. The control circuit 40 is also used to energize the fan 42.

The fan 42 can be used for providing control of gas or vapor content in the chamber atmosphere by directing a flow of air across a wick 44 that leads from a beaker 45 that contains suitable humidifying or environmental control liquid. The beaker 45 is held in place with a clip 45A mounted on the housing. The clip will hold a second beaker and wick if desired. The atmosphere can be maintained in a saturated condition to prevent evaporation, phase change, or other detrimental effects to samples or specimens to be examined. One or more humidistats or atmospheric condition sensors 47 are mounted at desired locations and the sensors 47 are used to control the fan 42 to direct airflow over wick 44 to change the saturation level of the controlled atmosphere. The wick 44 has a substantial surface area to enhance vapor transfer to the controlled atmosphere.

The bottom wall 27 of the housing is provided with an opening in which a self cocking photographic shutter assembly of conventional design indicated at 46 is mounted. A shutter sold under the trademark "Prontor" is satisfactory. The term shutter includes any generally openable and closable cover for the opening in the bottom wall.

The shutter 46 is a conventional photographic shutter that is of the iris type, and is self cocking. The shutter also can be of the type that is manually cocked with a lever or electronically or electrically actuated, and of either the iris type or gate type, if desired. The shutter 46 is tripped to open in a normal manner with an actuator cable 50 forming one cable of a dual cable shutter release. The details of the shutter and actuator cable are not shown, because they are conventional.

Figure 1:
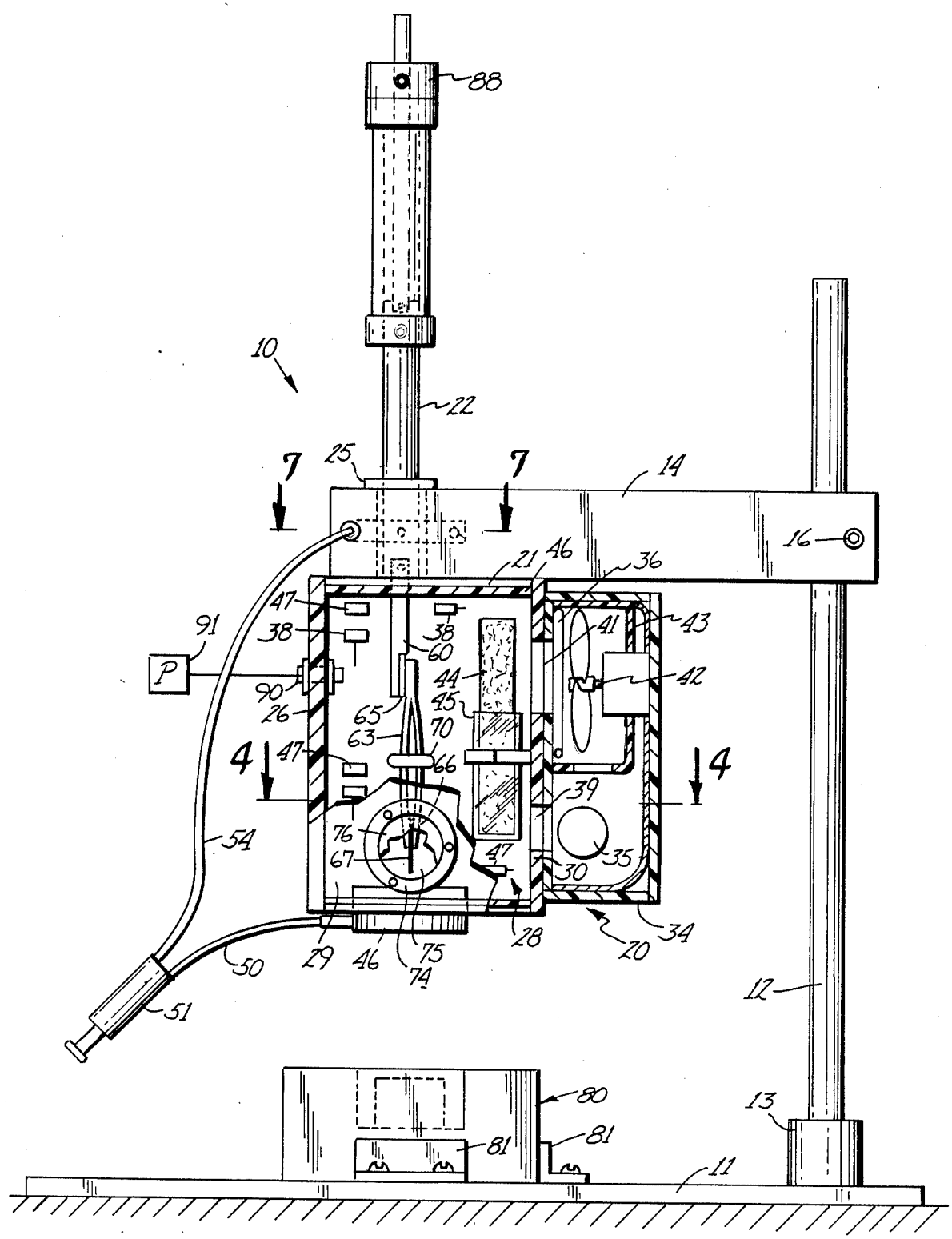
FIG. 1 is a side elevational view of a controlled environment vitrification apparatus made according to the present invention.
Figure 7:
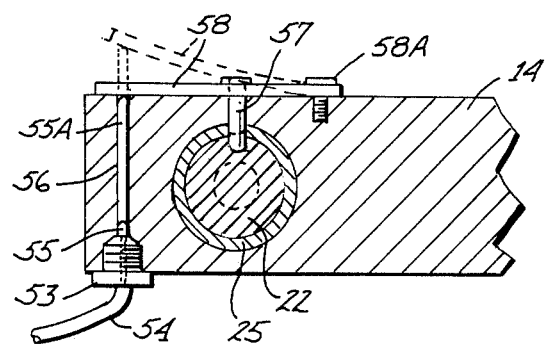
FIG. 7 is a fragmentary enlarged sectional view taken on line 7—7 in FIG. 1.

The cable 50 is connected to a manual plunger cable actuator 51. The actuator 51 is also used to simultaneously actuate a second release cable 54. The release cable 54 has an end connector 53 threaded into an end of a bore in arm 14 (see FIG. 7). An interior actuator wire 55 of the release cable 54 acts against the end of a pin 55A which is slidably mounted in a cross bore 56 on the outer end of the arm 14 adjacent the plunger shaft 22. The cable 54 and interior actuator wire 55 are used for controlling the dropping or plunging of shaft 22. The plunger shaft 22 has a recess in which a retainer pin 57 will fit when the shaft 22 is raised and aligned with the pin. As shown in FIGS. 1 and 7, the pin 57 is mounted on a leaf spring 58 that has one end held onto the arm 14 with a screw 58A. The free end of leaf spring 56 overlies the end of bore 56 and thus when the cable 54 is operated the pin 55A will push the end of leaf spring 58 outwardly as shown in dotted lines in FIGS. 3 and 7 to withdraw pin 57 from the shaft 22 to release the shaft for sliding or plunging. The timing of operation of the shutter opening and the release of shaft 22 is accomplished by adjusting the positions of the interior actuators in cables 50 and 54.

Upon actuation of the cable actuator 51, the cable 50 will open the shutter and cable actuator 55 will act on pin 55A to cause the pin 57 to be pulled out of the recess in shaft 22 to permit the shaft 22 to drop through the bushing or bearing 25, and as will be explained, plunge the prepared sample into a desired crogenic vitrification bath.

As can be seen on the interior of the chamber, as shown in FIG. 1 and in FIG. 5, the lower end of the shaft 22 has a tweezer mounting portion 60 that includes an offset shoulder 61 against which a tweezer head 62 of a tweezer assembly 63 can be positioned. The shoulder 61 and the head 62 can be arranged so that the tweezer can be precisely mounted, and as shown a magnet indicated at 65 is mounted on the tweezer so that it will attach magnetically to the shaft portion 60.

It should also be noted that a guide pin that precisely locates the tweezer can be used. When the specimen to be examined is going to be viewed immediately under a prepositioned microscope, mounting the tweezer precisely is of importance. A suitable collet also may be used for holding the tweezers in proper position. The tweezer 63 as shown has tweezer grip ends 66 that hold a specimen mounting grid or support plate 67 on edge. These grids or support plates are generally made of copper, and it can be seen that the plane of the specimen support plate substantially bisects the tweezer. The gripping ends 66 are held clamped with a suitable O ring or elastic ring indicated generally at 70 which can be slid upwardly to release the gripping points, or slid downwardly to its position as shown to grip the specimen support plate 67 securely.

The tweezers 63 are positioned on the mounting portion 60 so that the surfaces of the specimen support plate 67 are perpendicular to the side walls 29 of the housing. Each of the side walls 29 has flange 74 forming a port 75 therein in which a slit rubber septum 76 (a rubber diaphragm with slits in it) which minimize atmosphere exchange between the chamber and ambient atmosphere. These rubber septums are used for manipulating the specimen support plate and using a probe for adding the specimen material to the specimen support plate while leaving the environmental chamber closed. A pipette can be inserted through the septum and because the housing is transparent, the pipette may be operated to apply a liquid sample to the surface of the specimen support plate. The liquid sample may be stored in a small container 78, shown in FIG. 4, within the chamber 23. The sample is thus at the same temperature as the chamber. The pipette is used for transferring the sample from the container 78 to the specimen support plate 67.

Once a liquid sample has been placed on the specimen support plate, generally some filter paper or other suitably absorbant materials are used to remove excess liquid, or the liquid sample can be wiped, to leave only a very thin film of the solution or suspension on the specimen support plate to be examined under the microscope. Alternatively, the thin film can be formed by spontaneously wetting films, by dip coating the specimen support plate, or by "Kiss coating" which means touching the specimen support plate to a drop of liquid sample supported on another surface.

An insulated open top box indicated at 80 is positioned on the base plate 11, and is positioned immediately below the shutter 46. Suitable brackets indicated at 81 can be used for holding the box 80 aligned properly on the base plate 11, and in the interior chamber 82 of this insulated box, there are a pair of cups 83 and 84 that can be used for containing suitable materials into which the specimen is to be plunged for vitrification. The chamber 82 may be filled with liquid nitrogen or other cryogenic material to lower the temperature of solution in cup 83, which as shown is positioned below the shutter. The solution in cup 82 may be an melting ethane. The specimen is prepared as previously described into a thin layer on specimen support plate 67. The shutter release 51 is operated to release the pin 57 permitting the plunger shaft 22 to slide in the bearing 25 under gravity. Substantially simultaneously with or just slightly after release of the shaft, the shutter 46 will open, and the tweezer 63 carrying the specimen support plate and specimen or sample will plunge through the shutter opening along with the end of shaft 22 and drop immediately into the cup 83 (or cup 84, depending on which one is aligned in position), thereby vitrifying the specimen or sample without changing its microstructure due to atmospheric conditions.

The shaft 22 has an upper section comprising a threaded rod 87 that is pinned to the main shaft 22 and which extends upwardly therefrom. A sleeve having a lower collar 85 slides over shaft 22 and surrounds rod 87. A collar 88 is threaded on rod 87 and is used for adjusting the sleeve 86 to its desired position to provide a stop for shaft 22 when collar 85 engages the upper flange of bushing 25. The stop collar 85 provides a positive stop that can be precisely adjusted so that the specimen support plate 67, when positioned properly in the tweezer, for example with a locating pin or a stop shoulder on the tweezer gripping end 66, will drop to a predetermined fixed position. The speicmen may be plunged into the precise position necessary for examination with an electron microscope without moving the specimen to any substantial degree. The shaft 22 is biased by gravity to its second or plunged position because of its orientation. A spring can be used for loading the plunger shaft for plunging as well. The spring could be placed to act between top wall 21 of the housing and a collar on tweezer mounting portion 60 of the shaft, for example.

A nozzle 90 is provided on the housing to permit adding any desired gas or vapor and to provide a slight positive pressure in the chamber 23. The nozzle is connected to a suitable gas or vapor source 91. The source 91 can be any type of gas desired.

The apparatus is simple to use, and reliable. The specimen or sample is prepared in a controlled environment which prevents substantial changes in the microstructure of the specimen prior to vitrification, and thus reduces artifact formation.

After the specimen has been plunged into the vitrification medium, the tweezer can be removed from the plunger shaft 22 with suitable tongs and the specimen can be placed onto an electron microscope in its vitrified state and examined.

All necessary adjustments are possible to make the unit accommodate normal size specimen support plates, and also to insure that the plunging of the shaft 22 and the opening of the shutter 46 are timed appropriately.

The sensors for determining humidity, particular gas content, and temperature are available commercially. The showing is schematic because the particular environmental box configuration can vary at to where such sensors are located.

Although the present invention has been described with reference to preferred embodiments, workers skilled in the art will recognize that changes may be made in form and detail without departing from the spirit and scope of the invention.

What is claimed is:

1. A controlled environment specimen preparation apparatus comprising a base;
   a housing supported on said base in a spaced relationship thereto, said housing including wall means defining an interior chamber;
   means for controlling atmospheric conditions in said chamber;
   a shaft movably mounted with respect to said housing and having an end portion positioned within said chamber in a first position, and being movable to a second position with said end portion on the exterior of said housing, said shaft moving through an opening in one wall of said housing when moving from said first to said second positions;
   shutter means on said one wall aligned with said shaft and openable to permit said shaft to pass therethrough as said shaft moves from said first to said second position;
   means to urge said shaft to move from said first to said second position;
   means for releasably retaining said shaft in said first position;
   means for releasing said means for releasably retaining, and for opening said shutter means in a predetermined relationship to permit said shaft to move to said second position through said shutter means; and
   means for providing a cryogenic bath aligned with said shutter means to provide for vitrification of a specimen held by said shaft when the shaft moves to its second position.

2. The combination as specified in claim 1 and adjustable stop means to stop said shaft in said second position.

3. The apparatus as specified in claim 1 and means for providing addition of a gas to the atmosphere in the chamber, and sensor means for sensing the level of such control gas in said chamber.

4. The combination as specified in claim 1 and means for selectively supplying heating and cooling to said chamber in said housing, and sensor means for sensing the temperature within said chamber for controlling said means for selectively supplying heating and cooling.

5. A method of preparing a specimen under controlled environmental conditions comprising the steps of:
   providing an enclosed chamber having the desired environmental conditions;
   mounting a plunger for movement from a first position with a portion thereof within said chamber to a second position;
   providing a shutter openable for permitting said portion of the plunger to pass to the exterior of said chamber as it moves to its second position;
   providing a cryogenic material aligned with said shutter along the path of movement of said plunger;
   preparing a specimen within said chamber and mounting it on the plunger portion, and thereafter substantially simultaneously opening said shutter and permitting said plunger to move to its second position carrying a specimen into the cryogenic material.

6. The method of claim 5 wherein the step of opening said shutter includes the step of releasing said plunger against the action of bias means urging the plunger to its second position.

7. The method of claim 5 including the step of mounting the specimen within said chamber by manipulation of the specimen through a septum provided in a wall of said housing.

8. A controlled environment vitrification apparatus for preparing specimens comprising a frame;
   a housing mounted on said frame spaced above a portion of said frame, said housing forming a chamber and having means for permitting access to the chamber;
   environmental control means for controlling atmospheric conditions in the chamber to be in a desired state;
   plunger means movably mounted on said frame and including a portion within said chamber;
   means for mounting a specimen to be examined on said plunger means within said chamber, said means having a first position with a specimen held on the means for mounting in said chamber, and being movable to a second position; shutter means on a wall of said housing aligned with the path of movement said plunger means for selectively opening a passageway through said housing, said shutter means being openable to permit passage of a specimen held on the plunger means through the passageway to the exterior of said housing as the plunger means moves to its second position and being closable to close the passageway;
   means for biasing the plunger means to urge it to move to its second position; and
   release means for retaining the plunger means in its first position and for releasing the plunger means in response to a signal, the release means acting to open the shutter means at substantially the same time as the plunger means is released so a specimen may be moved through the passageway by movement of the plunger means to its second position.

9. A controlled environment vitrification apparatus for preparing specimens comprising a frame;
   a housing mounted on said frame spaced above a portion of said frame, said housing forming a environmental control means for controlling atmospheric conditions inside said housing;
   a plunger having a longitudinal axis slidably mounted on said frame and having a portion extending into said chamber;
   means for mounting a specimen to be examined on said plunger on the portion of the plunger in said chamber, said plunger having a first position with a specimen held on the means for mounting in said chamber, and being movable to a second position in a direction along the longitudinal axis of said plunger;
   openable and closable means on a wall of said housing aligned with the longitudinal axis said housing aligned with the longitudinal axis of said plunger for selectively opening a passageway through said housing, said openable and closable means being openable to permit passage of the plunger through the passageway to the exterior of said housing and closable to close the passageway;
   said plunger being urged to move from its first position in direction along its longitudinal axis toward said openable and closable means;
   latch means to hold said plunger in said first position; and
   release means for releasing said latch means and opening said openable and closable means substantially at the same time to permit the plunger to move through the passageway in the housing.

10. The apparatus as specified in claim 9 and stop means to stop movement of said plunger in said second position at a desired position along its longitudinal axis.

11. The apparatus as specified in claim 9 wherein said plunger is mounted with the axis substantially vertical so that gravity acts on said plunger to urge the plunger toward its second position.

12. The apparatus as specified in claim 9 and means for holding a vitrification medium on said frame in position aligned with the path of movement of the plunger as the plunger moves to its second position.

13. The apparatus as specified in claim 9 and sensor means for providing a signal to the environmental control means, said environmental control means including means for controlling the temperature in said environmental chamber in response to the signal from the sensor means.

14. The apparatus as specified in claim 1 wherein said means for mounting a specimen in position comprises a removable tweezer mounted on said plunger for clamping and holding a specimen support plate.

15. The apparatus as specified in claim 9 wherein said housing has side walls, and a slit septum in at least one of said side wall aligned with the location of a specimen held by the means for mounting a specimen to permit adding a specimen in the means for mounting through said septum.

16. The apparatus as specified in claim 10 wherein said stop means has means for adjusting the position thereof relative to the longitudinal axis of said plunger.

17. The apparatus as specified in claim 9 wherein said housing comprises two sections, one of said sections being fixed to said frame, and the other of said sections being mounted for sliding relative to the fixed section for permitting opening of the housing to provide access to the interior chamber.

18. The apparatus as specified in claim 9 wherein said environmental control means comprises sensor means to sense the temperature within said housing, and temperature control means coupled to said sensor means for controlling temperature in the chamber of said housing.

19. The apparatus of claim 18 wherein said environmental control means includes cooling means coupled to said sensor.

20. The apparatus of claim 18 wherein said environmental control means includes means to support a source of liquid to be changed to a vapor and added to the atmosphere within the chamber, a wick supported in said liquid and having a substantial exposed surface area, and fan means to direct a flow of fluid across said wick.

* * * * *

UNITED STATES PATENT AND TRADEMARK OFFICE
CERTIFICATE OF CORRECTION

PATENT NO. : 4,753,887
DATED : June 28, 1988
INVENTOR(S) : Jayesh R. Bellare et al.

It is certified that error appears in the above-identified patent and that said Letters Patent is hereby corrected as shown below:

In Column 9, delete lines 46-49 and insert therefore:

--a housing mounted on said frame spaced above
    a portion of said frame, said housing forming a
    chamber having means for permitting access to the
    chamber;
environmental control means for controlling
    atmospheric conditions inside said housing;--.

Column 9, lines 61-62, after "axis", delete "said housing aligned with the longitudinal axis".

Column 10, line 30, delete "claim 1" and insert --claim 9--; line 36, delete "wall" and insert --walls--.

Signed and Sealed this

Sixth Day of December, 1988

Attest:

DONALD J. QUIGG

*Attesting Officer*       *Commissioner of Patents and Trademarks*